United States Patent
Nudelman et al.

Patent Number: 5,955,624
Date of Patent: Sep. 21, 1999

[54] GROWTH STIMULATING FACTORS

[75] Inventors: Edward Nudelman, Seattle; Sen-Itiroh Hakomori, Mercer Island, both of Wash.

[73] Assignee: Cell Therapeutics, Inc., Seattle, Wash.

[21] Appl. No.: 08/473,901

[22] Filed: Jun. 7, 1995

Related U.S. Application Data

[63] Continuation of application No. 08/285,153, Aug. 3, 1994, abandoned.

[51] Int. Cl.[6] .................................................. C07C 57/00
[52] U.S. Cl. ............................ 554/227; 514/546; 514/547; 514/549; 514/552; 514/715; 514/722; 514/723
[58] Field of Search .............................. 554/227; 514/546, 514/547, 549, 552, 715, 722, 723

[56] References Cited

PUBLICATIONS

Foglia et al., Lipids, vol. 23, No. 5, pp. 430–434, 1988.
Seher et al., Thermal Anaylisi, vol. 3, pp. 109–121, 1971.

*Primary Examiner*—Gary Geist
*Assistant Examiner*—Deborah D. Carr
*Attorney, Agent, or Firm*—Stephen Faciszewski

[57] ABSTRACT

Alk-1-enyl glycerol derivatives and method of preparing same. The derivatives stimulate cell and tissue growth.

35 Claims, 3 Drawing Sheets

GROWTH STIMULATING FACTORS

This is a continuation of application Ser. No, 08/285,153 filed Aug. 3, 1994, now abandoned.

FIELD OF THE INVENTION

The instant invention relates to isolated fatty unsaturated ether derivatives of glycerol wherein said glycerol is substituted with at least one alk-1-enyl group. The compounds stimulate cell and tissue growth and find utility in promoting cell and tissue growth.

BACKGROUND OF THE INVENTION

Triglycerides are derivatives of glycerol wherein each of the hydroxyl groups of glycerol is derivatized by an ester linked fatty acid.

Glycerol derivatives comprising a single fatty unsaturated ether chain with an acyl group to form a diglyceride have been suggested by observing degradation products from cleavage of phosphoplasmalogens and may be the result of enzymatic cleavage of phosphoglycerides, such as by phospholipase C.

Bass et al. (J. Biol. Chem., 264, 19610–19617, 1989), demonstrated that an alkyl-acyl diglyceride had the paradoxical effect of activating the respiratory burst of polymorphic mononuclear leucocytes at low concentrations and inhibiting the respiratory burst at high concentrations. Veldhoven et al., Biochem. Biophys. Res. Comm., 187, 209–216, 1992, demonstrated that levels of alkylacylglycerol were elevated following HIV infection of CEM cells and suggested that such molecules may fulfill a mediator role of unknown mechanism.

The omentum is known to mediate inflammatory responses and to stimulate angiogenesis. Vineberg et al., Can. Med. Assoc., 90, 717–722, 1964; Goldsmith et al., Arch. Surg., 106, 695–698, 1973.

The lipid composition of omentum has been investigated. Rabinowitz et al., Lipids, 13, 317–322, 1978; McCluer et al., Lipids, 22, 229–235, 1987 and 24, 951–956, 1989.

SUMMARY OF THE INVENTION

The instant invention provides novel glycerol derivatives comprising at least one fatty unsaturated ether side chain, also known as an alk-1-enyl ether group, to yield novel triglyceride, diglyceride or monoglyceride compounds.

The monoalk-1-enyl ether derivatives have the following formula:

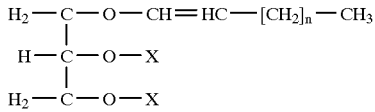

wherein n is 0–23 and X is H or an acyl group wherein the number of carbon atoms is from 2 to 26.

The invention provides also dialk-1-enyl derivatives of the following formula:

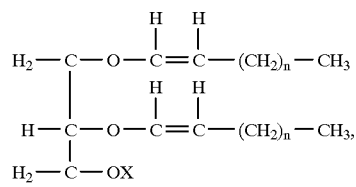

wherein X is H or an acyl group wherein the number of carbon atoms is from 2 to 26 and n is 0–23.

The invention further provides trialk-1-enyl derivatives of the formula:

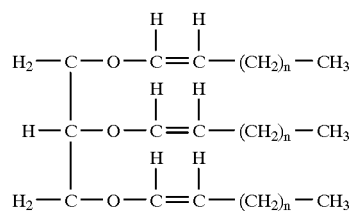

wherein n is 0–23.

The alkenyl and acyl side chains may be unsaturated, and at more than one site.

The instant alk-1-enyl ether glycerides promote the growth of cells and tissues.

Moreover, the instant invention provides a novel method for purifying the above compounds from tissues.

DETAILED DESCRIPTION OF THE INVENTION

Figure 1:
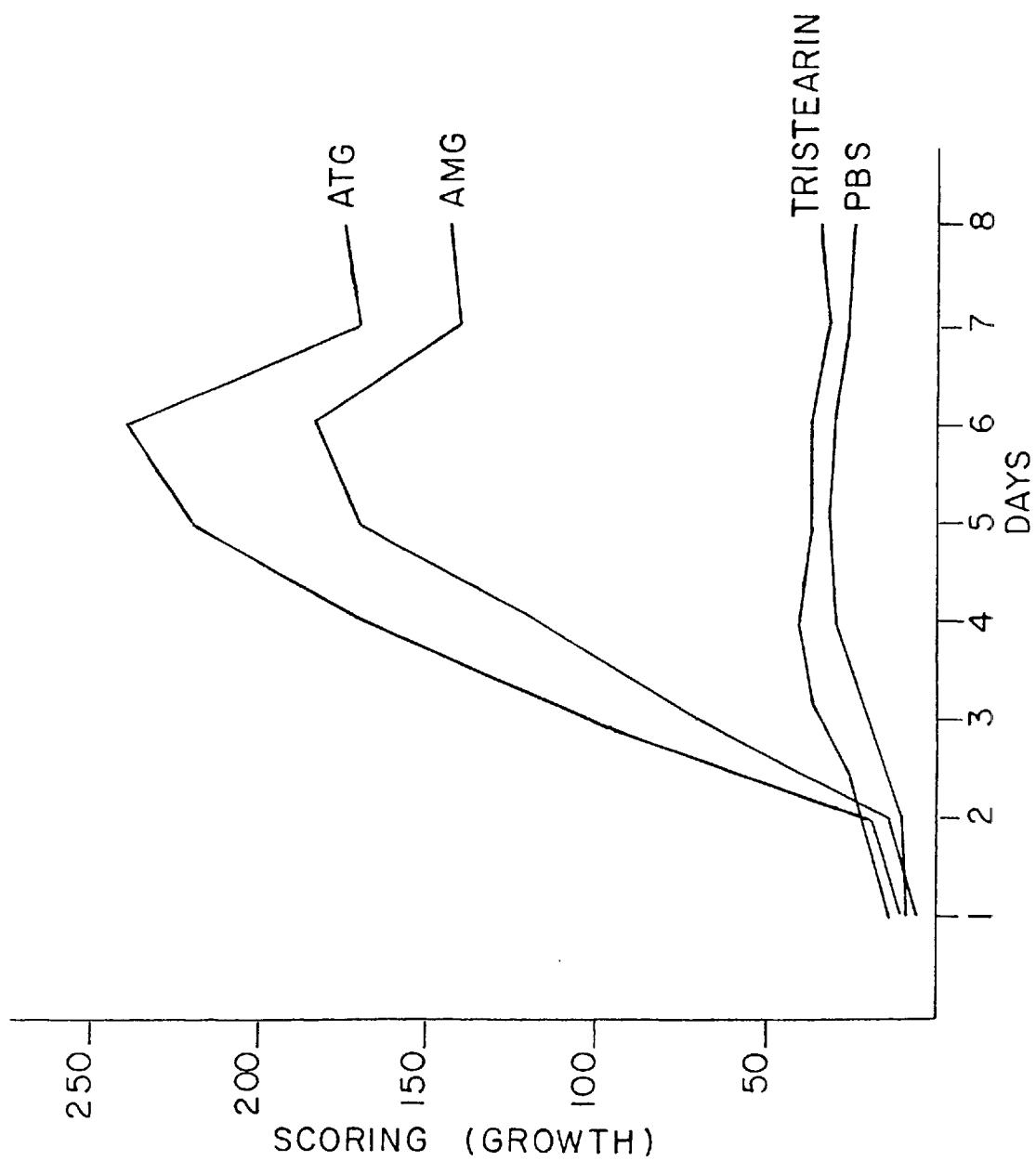
FIG. 1 depicts the effect various compounds have on microvessel growth. PBS is phosphate-buffered saline. AMG is alk-1-enyl monoglycerol. ATG is alk-1-enyl triglycerol. The ordinate depicts the degree of vessel growth observed microscopically.

As used herein, "isolated", indicates some intervention to provide at least a de minimis level of purification over the state of the compound found in situ. "Isolated" is meant to indicate that the instant active agent is not present in its natural state or surrounding, that is, some manipulation occurs to obtain enhanced level of purity over that found in nature.

Moreover, a derivative of the instant active agent is, for example, a physiologically acceptable salt thereof, a homologue thereof, an analogue thereof, an isomer thereof and the like so long as said derivative retains at least about one-fourth of the cell and tissue growth stimulating activity of the parent compound of the derivative, as defined with respect to the assays taught herein.

A derivative with a higher level of activity than the parent compound is desirable, however a derivative with a lower level of activity than the parent compound but endowed with other desirable characteristics, such as water solubility or long serum half-life, also is contemplated to fall within the scope and spirit of the instant invention.

The instant active agents have a variety of cell and tissue growth stimulating activities manifested, for example, as angiogenesis and neuritogenesis.

The instant active agents are novel glycerol derivatives comprising at least one side chain comprising an ether-containing hydrocarbon. The ether group generally is located at the one position of glycerol. The hydrocarbon chain can contain up to twenty-six carbon atoms. That is, referring to the formulae hereinabove, n is 0–23. Thus, n can be 13 or 15, as in exemplified compounds.

The ether groups are related to the fatty acids. Hence, synthesis of the instant compounds may rely on the use of known fatty acids and other hydrocarbons comprising a carboxyl group.

Structures with one ether group and no acyl groups are known as alk-1-enyl monoglycerides (AMG); those with one ether group and one acyl group as alk-1-enyl diglycerides (ADG); and those with one ether group and two acyl groups as alk-1-enyl triglycerides (ATG).

Hence, of the monoalk-1-enyl compounds, an AMG has the following structure:

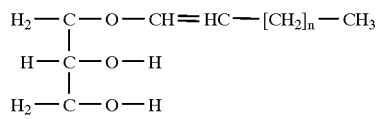

wherein n is 1–23. The ether group can be at the 2-position of glycerol.

An ADG has the following structure:

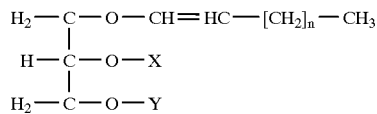

wherein n is 1–23 and one of X and Y is H and the other is an acyl group. The ether group can be at the 2-position of glycerol.

Finally, an ATG has the following structure:

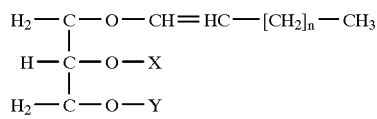

wherein n is 1–23, each of X and Y is an acyl group and X and Y may be the same.

The instant compounds can comprise one or two acyl groups. Generally, the acyl groups are obtained from the naturally occurring fatty acids and hence have hydrocarbon chain lengths of up to 26, that is, in the formulae above, m is 1–24. The acyl groups can comprise one or more sites of unsaturation.

A compound of interest is one containing a $C_{20}$ acyl group having four double bonds. Included in that class of fatty acid derivatives is arachidonic acid, a molecule integral in the leukotriene-prostaglandin pathway.

Hence, a compound of interest is a monoalk-1-enyl comprising arachidonic acid. Suitable alk-1-enyl substituents are those wherein n is 13 or 15.

Another preferred group of compounds is ATG comprising arachidonic acid as one acyl group. The other acyl group can be arachidonic acid or another fatty acid derivative.

An additional group of compounds of interest are those wherein the alk-1-enyl group is of a $C_{16}$ or $C_{18}$ species, that is n is 13 or 15 in the above formulae.

Angiogenesis is the process by which new blood vessels are formed. Normal growth, differentiation, wound healing, autoimmune phenomena, establishment of the placenta and extraembryonic membranes and the like are accompanied by new blood vessel formation, also known as, neovascularization (Folkman & Klagsbrun, Science, 235, 442–445, 1987; Klagsbrun & D'Amore, Ann. Rev. Physiol., 53, 217–239, 1991). In disease states, angiogenesis plays a role in, for example, tumor development where an adequate blood supply helps promote the viability of the aberrant growth.

The instant invention also provides a novel method for purifying lipids of interest from biologic sources. Because of the predominance of simple acylated triglycerides in many lipid preparations of biologic origin, particularly, those which yield the instant active agents, purification of lipids of similar structure to the triglycerides but present in small amounts is impossible. Heretofore, it has not been possible to isolate and thus purify the compounds of interest.

The instant compounds may be purified from tissue sources known to support cell and tissue growth, such as the omentum and placenta.

Generally, a suitable tissue is homogenized in a suitable organic solvent, such as a 2:1 ratio of chloroform:methanol. The filtrates are pooled and evaporated using ethanol to assure removal of water. The extracts are further evaporated with excess toluene to remove all traces of ethanol.

The residue is suspended in toluene and then applied to a column comprising FLORISIL™ (activated magnesium silicate, Sigma Chemical). The column is washed profusely with toluene, for example, at least five bed volumes. Then, the column is eluted with a dichloroethane:acetone gradient and fractions are collected.

The novel purification scheme involves fractionation over FLORISIL™ beads and elution of the normal triglycerides by 100% toluene. Using that method, pure triglyceride was eluted almost quantitatively with no elution of more polar lipids. Further elution of the column with dichloroethane allowed for the near quantitative elution of cholesterol. Elution with a 96:4 ratio by volume of dichloroethane to acetone enabled elution of lipids with enhanced cell and tissue growth stimulating activity. That fraction contained the alk-1-enyl derivatives of the instant invention. Elution of the column with 100% acetone yielded nearly quantitative recovery of the monoalk-1-enyl glycerides.

The collected fractions can be purified further using, for example, preparative separation in suitable solvents using high performance thin layer chromatography as well as high performance liquid chromatography.

Alternatively, the instant compounds can be synthesized by chemical and/or enzymatic means. For example, brain or beef heart ethanolamine glycerophospholipids, commercially available or which can be purified using known methods, are de-acylated by alkaline methanolysis. The reaction mixture is neutralized and mixed gently in a separatory funnel. The lower phase is collected and dried under vacuum.

The resultant oil is dissolved in chloroform, applied to an HPLC column and a chloroform to methanol gradient is used to elute the column. Lysoplasmenylethanolamine (LPE) is obtained in near homogeneous state.

LPE is treated with phospholipase C (commercially available or obtained by known purification methods) which cleaves the phosphatidyl group at the proximal oxygen. The resulting AMG is purified by HPLC using a toluene to acetone:ether (80:20) gradient.

To obtain ADG, LPE is protected by blocking the polar phosphatidyl functional group using, for example, N-9-fluorenylmethoxycarbonyl (Fmoc) using standard methods. To the protected LPE in DMAP (dimethylaminopyridine) is added the appropriate fatty acyl anhydride or acyl chloride in molar excess. Dicylohexylcarbodiimide is added to regenerate the anhydride.

The reaction is terminated by addition of diethylamine. The resulting plasmenylethanolamine (PPE) is purified and treated with phospholipase C to cleave off the phosphatide group between the proximal oxygen and phosphorus atoms yielding the hydroxyl group of glycerol.

To obtain ATG, AMG is acylated with the appropriate fatty acyl anhydride or acyl chloride and purified by HPLC.

The specific target compounds, isolated and purified as disclosed herein, can be identified and tracked during purification or synthesis by monitoring the biologic activities thereof.

Hence, the angiogenic activity can be monitored by assessing microvessel growth in tissue explants or in vivo.

The instant compounds also demonstrate neurotogenic activity. Neuroblastoma cells are used widely to screen substances having possible promoting effects on neuritogenesis, particularly as predictive of use as drugs. A summary of the relevance of in vitro studies is presented in Samson, Drugs of Today, 22(2), 73–104, 1986.

The nerve cells are cultured in gelatin-coated plates by known methods, (Canella et al., Dev. Brain Res. 39, 137–142, 1988; Int. J. Dev. Neurosci. 6, 319–326, 1988). The effective dose is determined by adding various concentrations of one or more of the instant derivatives and the cells are cultured for the observation of neurite formation.

The instant active agents can be used to maintain and to enhance growth of cells and tissues in vitro, for example, enhance the storage time of tissues awaiting transfusion or transplantation or to seek purposefully growth of cells, tissue rudiments and tissues in vitro preparatory to transplantation.

To accomplish such, normal cell culture and tissue culture methods are practiced, for example, using standard media, such as RPMI 1640, Eagle's MEM, Ham's Flo and the like which may be supplemented with various amounts of serum, such as fetal bovine serum or calf serum, in amounts ranging from 1% up to as much as 25%, or the cells and tissues may be cultured under serum-free conditions in specialized media supplemented with various essential nutrients, such as transferrin and growth factors.

To the culture medium is added amounts of the instant active agents to maintain or to promote growth. The active agents, if not soluble in aqueous media, first are dissolved in a minimal amount of organic solvent, such as ethanol, and the dissolved solution then is suspended in a volume of medium identical to that used in the culture of the cells or tissues to be treated. Sonication may be required to place the instant active agents totally in solution. The active agents then are added to the culture medium and can be replenished at regular intervals either as a supplement or as a component of the culture medium.

The compounds also find use in a variety of other applications requiring cell and tissue growth. For example, the instant compounds can be used to stimulate would healing by application to the wound site. The instant compounds can be used to enhance engraftment, for example, growth of a skin transplant at the graft site. The instant compounds also can be used to enhance the healing process in patients with burns and particularly severe burns.

The instant compounds demonstrate neurotogenic activity as demonstrated using a known model for lipid drugs. Hence, the instant active agents will find use when neural tissue development is desired.

A summary of the relevance of in vitro studies to anticipated in vivo use is presented in Samson, Drugs of Today, 22(2), 73–104, 1986.

The instant invention provides a method for treating neuronal diseases and tissue damage comprising administering to a host in need of treatment a biologically effective amount of one or more of the instant derivatives and pharmaceutically acceptable salts thereof.

Specific cases include treatment of Alzheimer's disease, spinal injury such as paralysis, cerebral vascular accidents where there is loss of neural tissue, brain trauma, Parkinson's disease, amyotrophic lateral sclerosis and multiple sclerosis.

The instant glycerol derivatives are detectable by, for example, mass spectroscopy, thin layer chromatography, immunoassay and the like. Detection of the instant glycerol derivatives is mandated in situations when the metabolism of said derivatives is aberrant and abnormal. It is known that mutation of growth factors can result in malignant transformation; loss of or lack of functional clotting factors can result in bleeding disorders; poor circulation can result in gangrene; and the like. The same applies for the instant glycerol derivatives where aberrant growth or chronic wounds can arise from aberrant glycerol derivatives metabolism.

Mass spectroscopy or thin layer chromatography are not well-suited to a clinical or hospital laboratory where rapid often only qualitative results are needed. In such circumstances, often an antibody-based assay is more suitable.

A purified glycerol derivative of the instant invention is provided in a physiologic buffer and administered to a host. An adjuvant, such as Freund's complete or incomplete adjuvant, or carrier, such as keyhole limpet hemocyanin, can be used to enhance immunogenicity, as well as other known means and methods. The immunization schedule and routes can be determined by the artisan. Any of a variety of stimulation regimens can be used.

After a suitable stimulation period the host is bled, serum obtained and can be used outright. The antiserum can be absorbed with cross-reactive substances to obtain a "monospecific" or more specific antiserum.

Alternatively, hosts suitable for making monoclonal antibodies, such as a mouse, can be stimulated. Following appropriate stimulation, the spleen is removed and the splenocytes used for fusion with myeloma cells. A suitable screen would be an ELISA using the cognate antigen as the solid phase-based antigen.

The antibody, polyclonal or monoclonal, then can be used in an immunoassay for determining presence and amount of cognate antigen in a sample, such as a liquid tissue, such as blood; a tissue extract obtained by cell lysis to yield a soluble aqueous fraction; spent medium from a cell or tissue culture; and the like.

The antibody can be bound to a solid phase, such as the inside wall of a vessel or an inert matrix bead. A positive reaction can be monitored with a second labelled antibody in a sandwich assay or by flocculation or precipitation. How to configure an assay is well within the skill of the artisan.

Additional ganglioside and glycerol phospholipid fractions obtained from, for example, omentum facilitate or potentiate the stimulating activities of the instant compounds. For example, a disialyl ganglioside from omentum triples the activity of ATG and ADG in the in vitro angiogenesis assay described hereinbelow. That same compound potentiates the activity of AMG ten-fold in the in vitro assay using rat aortal rings.

Hence, in the various uses and formulations comprising the ether derivatives of the instant invention, combined use with such other gangliosides or glycerol phospholipids is contemplated.

A suitable ganglioside found in the omental disialyl ganglioside fraction is GD3 with the structure, NeuAc2→8NeuAc2→3Gal1→4Glu1→1Cer.

For example, omentum and bovine milk are suitable sources of GD3. The tissue is homogenized in chloroform-methanol (2:1) solvent and filtered. The filtrate is allowed to dry and partitioned in Folch (6 parts chloroform: methanol (2:1) and one part water).

The upper phase is removed, dried by rotary evaporation, resuspended and passed over a DEAE column. The disialyl fraction is obtained in 0.15 M ammonium acetate in methanol. The fraction is dialyzed and exposed to repeated HPLC Iatrobead chromatography until pure.

A suitable glycerol phospholipid is one where either or both hydroxyl groups remain unsubstituted. The phosphate group can be derivatized with a group comprising a hydroxyl group. A suitable example is lysophosphatidyl serine:

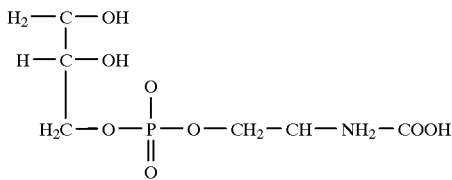

Lysophosphatidyl serine can be used in conjunction with an ether glycerol derivative of the instant invention as a potentiator of the ether derivative activity.

The instant invention further provides medicaments and treatments for enhancing growth of cells and tissues:

(1) a therapeutically effective amount of the instant active agents or pharmaceutically acceptable salts thereof; and (2) a pharmaceutically acceptable carrier, diluent or excipient.

The medicament comprises an effective amount of the instant active agents and a pharmaceutically acceptable carrier, diluent or excipient. The effective amount of the instant active agents can be determined using art-recognized methods, such as by establishing dose-response curves in suitable animal models, such as described herein or in non-human primates, and extrapolating to human; extrapolating from suitable in vitro data, for example, as described herein; or by determining effectiveness in clinical trials. The medicament can contain such potentiating gangliosides and glycerol phospholipids described hereinabove.

Suitable doses of medicaments of the instant invention depend upon the particular medical application, such as the severity of the disease, the weight of the individual, age of the individual, half-life in circulation etc., and can be determined readily by the skilled artisan. The number of doses, daily dosage and course of treatment may vary from individual to individual. Generally, individual doses are on the order of nanogram to microgram amounts. In a topical formulation the dosage generally is increased by about two to three orders of magnitude into the microgram to milligram range. If a potentiator is used, a suitable amount of potentiator is in the microgram per milliliter range. In topical preparations, the amount is increased by about two to three orders of unaguitude, for example, 100 μg. of potentiator per ml. or mg. of preparation.

The instant active agents can be administered in a variety of ways such as orally, parenterally and topically. Suitable pharmaceutically acceptable carriers, diluents, or excipients for the medicaments of the instant invention depend upon the particular medical use of the medicament and can be determined readily by the skilled artisan.

The medicament can take a variety of forms such as tablets, capsules, bulk or unit does powders or granules; may be contained within liposomes; or may be formulated into solutions, emulsions, suspensions, ointments, pastes, creams, gels, foams or jellies. Parenteral dosage forms include solutions, suspensions and the like. The medicament is likely to contain any of a variety of art-recognized excipients, diluents, fillers etc. Such subsidiary ingredients include disintegrants, binders, lubricants, surfactants, emulsifiers, buffers, moisturizers, solubilizers and preservatives. For example, mineral oil, methyl paraben, cholesterol, petrolatum and waxes may be used for a topical preparation. The artisan can configure the appropriate formulation comprising instant active agents and seeking guidance from numerous authorities and references such as "Goodman & Gilman's The Pharmaceutical Basis of Therapeutics" (6th ed., Goodman et al., eds., MacMillan Publ. Co., NY, 1980).

In body sites that are relatively inaccessible, instant active agents can be administered in a suitable fashion to assure effective local concentrations. For example, instant active agents may be injected in a depot or adjuvant, carried in a surgically situated implant or reservoir that slowly releases a fixed amount of instant active agents over a period of time or may be complexed to recognition molecules with the capability of binding to the site presenting with abnormal cell growth. An example of such a contemplated scenario is a recognition molecule, such as an antibody with binding specificity to the site of interest wherein said antibody is complexed to instant active agents, said complex administered to a patient.

By topical it is contemplated that the instant factors can be exposed to or applied to an epidermal or epithelial surface. Generally topical indicates to the skin or external portions of an organism, such as serous membranes, for example within the eye socket, nares, auditory canal, urinary tract, reproductive tract and the like. However, topical also may indicate a regional or local application to body cavities by, at or through various orifices, such as the ends of the digestive tract, that is, the oral cavity and the rectum.

The glycerol derivatives find therapeutic utility in circumstances that require cell growth, such as growth enhancement or wound healing. In the case of epidermal abrasion, laceration, bed sores, broken bones, puncture or other lesion, the factors can be administered directly to the wound site in the form of, for example, a liquid, gel or cream, in established effective amounts. The glycerol derivative preparation can be administered singly or in a plurality of treatments, and in combination with other growth agents.

Alternatively, the glycerol derivative can be added as a supplement to known pharmaceutic, prescription, over the counter and the like preparations with known mitogenic, angiogenic, nucleic acid synthesis stimulating, cell growth, cell proliferation and the like activities, which for the purposes for the instant invention are considered in toto as "growth agents". Hence, the instant derivatives can serve as additive, potentiators, enhancers, adjuvants and the like for the existing activities of the known preparations.

For example, the glycerol derivatives of the instant invention can be added to known preparations comprising live yeast cell derivative or an alcoholic extract of live yeast cells.

Moreover, the factor(s) of the instant invention can be combined with other growth factors, mitogens, cytokines, hormones, somatomedins, differentiation factors and the like agents which stimulate cell, tissue, organ or organismal proliferation or growth. While the end result of the action of such factors may be varied, such as increase in mass, weight, cell number and the like, it is contemplated that at the root of such physiologic activities is the synthesis of nucleic acid and more specifically of genomic nucleic acids or messenger-type nucleic acids. Hence, for the purposes of the instant invention, all of such factors disclosed in and referred to in the instant application, which are best typified by stimulating nucleic acid, and generally DNA, synthesis, will be categorized as "growth agents".

Some examples of such agents include lymphokines, epidermal growth factors, angiogenic factors, fibroblast growth factors, nerve growth factors, platelet-derived growth factors, transforming growth factors, insulin-like growth factors, colony stimulating factors, pokeweed mitogen, phytohemagglutinin, concanavalin A, lipopolysaccharide, various other lectins, keratinocyte growth factors, endothelial cell growth factors, stem cell factors, tumor necrosis factor, erythropoietin, insulin, growth hormone, steroids, retinoic acid, butyric acids, interferons, interleukins, somatomedins and the like. Such agents are available commercially from sources such as Boehringer-Mannheim, Genentech, Amgen, Miles, Sigma, Chiron and the like being made by biochemical purification of natural source material or by recombinant means. A non-exhaustive exemplification of uses of the factor(s) is set forth hereinbelow.

All products listed can be used, for example, in a lotion, cream, ointment, spray, liquid, topical dressing or vehicle.

Burns
Sun
Wind
Mechanical
Oil/Grease
Water
1st, 2nd and 3rd Degree Burns
Chemical
Wounds
Superficial, e.g., minor chapped lips and blisters
Partial Thickness e.g., minor cuts and scrapes
Abrasions
Paper cuts
Insect Bites
Full Thickness, e.g., gunshot wounds
Lacerations
Dermabrasions
Skin Grafts
Vascular
Cosmetic Surgery
Chronic e.g., diabetic ulcers, venous stasis, ulcers, pressure sores

| Topical Indications | |
|---|---|
| Diaper Rash | Psoriasis |
| Heat Rash | Seborrhea |
| Frostbite | Rosacea |
| Dermatitis | Bed Sores |
| Chafing | Decubitas Ulcers |
| Poison Ivy/Oak | Nail Growth |
| Warts | Hair Growth |
| Acne | Dandruff |
| Athletes Foot | Alopecia |
| Jock Itch | Hemorrhoids |
| Photo-aged Skin | Herpes and other |
| Wrinkles | infections |
| Varicose Veins | Itching |
| Stretch Marks | Vaginal Irritations |

Oral Indications
Oral Ulcerations
Cold Sores
Gingivitis
Herpes
Periodontal Disease
Internal
Gastric Ulcers/Irritations
Bowel Dysfunction
Tracheal Burns
Nasal Membranes
Esophagitis
Other
Sprains, Strains, Tendinitis
Arthritis
Hairloss e.g. Acopecia areata, Chemotherapy
Dressings
Transdermal Delivery System
Mucoadhesive Delivery System
Band-Aid
Burn Pad with Water
Acne Pad
Hospital and Surgical Dressing
Combination Products with the Instant Factors
Shaving Cream
Aftershave
Makeup Remover
Toothpaste
Depilatory
Waxing
Shampoo
Conditioner
Perming Solution
Mousses
Mouthwash
Denture Adhesive
Soap
Nail Polish
Face Mask
Douches
Lip Balms
Bath Oil The ether glycerol derivatives will find utility in parts of the body characterized by low circulation. Such sits include, for example, the limbs of a diabetic patient, a patient having experienced a stroke or afflicted with coronary artery disease, or following a traumatic injury.

A key feature of the molecules of the instant invention is the unsaturated ether and more specifically the double bond adjacent to the etheric oxygen. If the double bond is removed, the compound no longer is active but can be used as an antagonist, that is, the compound not only blocks the activity of the instant active agents but can reverse the activities of the instant active agents.

Thus compounds lacking the unsaturated bond adjacent to the etheric oxygen can be used to control rampant and apparently uncontrolled cell and tissue growth, such as observed in endometriosis, autoimmune disorders, psoriasis, cancer, retinopathies, benign tumors, goiter, prostatic hyperplasia and the like.

The invention now will be described by way of the following non-limiting examples.

EXAMPLE 1

Adult human omentum, obtained at autopsy and frozen at −40° C., within 8 hrs. post mortem, was thawed and cut into small pieces, washed briefly with water and patted dry. The tissue, typically 2 kilogram preps, was homogenized in a large Waring blender with four volumes (i.e, four times volume/weight of wet tissue) of chloroform-methanol (2:1), filtered over a Büchner funnel, and the residue re-homogenized in the same solvent and filtered two additional times. The three clear, yellow filtrates were pooled and evaporated to dryness by rotory evaporation using absolute ethanol to rid the sample of water. The oily extracts were further evaporated several times with excess toluene to assure no ethanol remained. The final organic extracts were brought up in toluene to a final volume/weight (liters/kg.) of original wet weight.

A column of FLORISIL™ (Sigma, 60–100 mesh) was prepared as follows: 200 grams Florisil per 1 kg. wet weight of tissue was equilibrated by pouring into excess toluene and swirling for several minutes. The florisil was poured into a large, cylindrical glass column containing about twice the volume of toluene and allowed to elute until the florisil had settled and 1 column volume had passed through. The total organic extract was applied to the top of the column and allowed to elute by gravity. After the last of the extract had entered the bed, the column was washed with 5 column volumes of toluene, collected separately from the original pass through fraction. The column was subsequently eluted and fractions collected as follows (about 4 liters per fraction for typical 2 kg. prep): dichloroethane, dichloroethane/acetone (96:4), dicloroethane/acetone (90:10), acetone, chloroform/methanol (2:1), isopropanol/hexane/water (55:25:20). Each fraction was evaporated to dryness by rotary evaporation and the resulting samples transferred to screw cap vials using chloroform/methanol (2:1).

The FLORISIL™ fractions were assayed for angiogenesis and neuritogenesis and those fractions possessing activity were further purified as follows. A large column (5 cm.×100 cm.) packed with Iatrobeads (Iatron, Toyko, Japan) (10 uM) was equilibrated as follows. Elution began with 100% toluene at 5.0 ml./min. and a gradient elution sustained over 45 min. up to 100% acetone, followed by a gradient elution for 45 min. up to chloroform/methanol (2:1) and maintained isocratically for 30 min. The elution profile was repeated inversely, returning to the initial solvent of 100% toluene.

The FLORISIL™-eluted sample was carefully prepared for injections as follows. The sample was evaporated to dryness by rotary evaporation using excess toluene (4–5 aliquots of several hundred mls.). In some cases, the sample was diluted 1:1 in toluene, and applied to the equilibrated column in separate injections of 10 ml. each, allowing for elution of about 15 mls. between the next injection. The initial flow rate for sample applications was 2.0 ml. per minute.

For a typical 2 kg. prep, the volume for injection was about 40 mls. Angiogenic capacity was found to be highest in the dichloroethane/acetone (96:4) fraction, which contained ATG. The gradient elution scheme for maximal purification of ATG was as follows. The sample was loaded onto the column into a 10.0 ml. sample loop and injected at an initial flow rate of 2.0 ml./min. in four boluses as described above. After application of the entire sample, the flow rate was reduced to 1.0 ml./min. and a gradient elution proceeded up to 500 min. The solvent is composed of two solutions, A and B. Solution A comprises a 60:40:5 solution of hexane:ether:acetone. Solution B comprises a 90:10:1 solution of chloroform:methanol:ammonium hydroxide. Solutions A and B are mixed in a ratio of 4:1. The solvent composition remained isocratic over the last 100 min., whereupon the flow was stopped at t=600 min.

In some cases, where more polar fractions were applied, the elution gradient proceeded as follows. Following the 600 min. elution scheme above and considering t=0 min., a gradient to 100% acetone was maintained up to t=200 min., elution sustained isocratically up to t=300 min., followed by gradient elution to 100% chloroform/methanol (2:1) up to t=500 min., and finally the elution was sustained isocratically up to t=600 min.

The final purification of ATG is obtained using a sensitive fuschin-sulfite reagent, such as Schiff's reagent, Sigma, for the detection of aldehydes obtained by the acid hydrolysis of the fatty unsaturated other group which is converted to an aldehyde. Fractions from the HPLC chromatography above were pooled based upon the positive staining with the fuschin reagent as follows. HPTLC plates (Whatman) were spotted with fractions from the HPLC, dried and sprayed with a fine mist of a 15% fuschin solution in water and the plate allowed to air-dry with slight heating by hair dryer. The positive reaction, detected visibly by the appearance of a blue/violet-blue color, was distinctive for the fatty-unsaturated ether group, which liberates the free aldehyde on contact with the reagent.

Using that technique, two major positive bands, designated ATG1 and ATG2 were pooled from the HPLC fractions of the dichloroethane/acetone (96:4) fraction. Four other less abundant fuschin-positive bands were found in the (96:4) fraction, designated ATGa, ATGb, ATGc and ATGd. Several additional fuschin positive bands were found in the HPLC fractions of the dichloroethane/acetone (90:10) and also 100% acetone. No other fuschin positive bands were present in any of the other Florisil fractions.

Purification of the target compounds was obtained by preparative HPTLC in specifically designated solvent systems. The method involved preparatively streaking 100–200 micrograms semipure pooled HPLC fractions of ATG1 and ATG2 mixtures onto Merck HPTLC plates and chromatographed. Species are identified by staining with primuline, a fluorescent dye, Aldrich. Addition of small quantities of base enabled recovery of two species of ATG1 and ATG2.

To obtain ATG, a solvent of 9:1 hexane:ether was used. For ADG a hexane:ether:acetone solvent (60:40:5) was used. For AMG, a chloroform:methanol:ammonium hydroxide (90:10:1) solvent was used. To obtain GD3 and lysophosphatidyl serine, a solvent of chloroform:methanol:water (50:40:10) with 0.05% calcium chloride was used.

Base treatment to liberate free fatty acids was accomplished by dissolving sample (20 Ag.) in 75 microliters of chloroform/methanol (2:1) and adding 25 microliters of a 1% solution of sodium methoxide in methanol (final concentration of 0.25% sodium methoxide) and the sample allowed to remain at room temperature for 30 min. Slightly harsher conditions used were 0.3N NaOH in MeOH at 80° C. for 30 min. Weak acid treatment as catalyzed by mercuric chloride (0.1% $HgCl_2$ in 0.1 N HCl) was performed according to the original method of Feulgen et al. (Feulgen, R., Imhauser, K., and Behrens, M. (1929) Hoppe-Seyler's Z. Physiol. Chem. 2:161–180); alternatively, sample was treated in 0.3 N HCl in MeOH at 80° C. for 30 min.

FAB-MS was performed on a JEOL (Tokyo, Japan) HX-10/DA-5000 mass spectrometer/data system, operated in the accumulation mode at full acceleration voltage (10 kV); xenon beam 6 kV; resolution 3,000 aliquots of sample (20 microgram) in MeOH was transferred to a FAB target and suspended in an appropriate matrix. Native lipid samples were analyzed by FAB-MS using 3-nitro-benzyl alcohol (NBA) matrix, with and without addition of sodium acetate. The mass range was m/z 100–2,000. Three scans were accumulated for each spectrum. Sodium iodide in glycerol was used as the calibration standard.

EXAMPLE 2

The in vitro angiogenesis method is an adaptation of Nicosia & Ottinetti who established a three-dimensional model of microvessel growth in various matrices, such as fibrin and collagen (Nicosia, R. and Ottinetti, A. (1990) "Growth of Microvessels in Serum-Free Matrix Culture of Rat Aorta." Lab. Inves. 63:115–121). Primary explants of rat aorta (1 mm. thick rings) could generate branching microvessels in the absence of serum or other soluble protein supplements, especially when grown in fibrin. The model worked well as an assay for determining angiogenesis in unknown samples when collagen was used, as the non-specific formation of vessels was quite low on that matrix.

Thoracic aorta from 1–2 month old Fischer male rats were obtained after sacrificing the animals in a $CO_2$ chamber. The aortae were cleaned of the fibroadipose tissue using a dissecting microscope and fine forceps and scissors, and then cut into 1 mm. sections or rings. About 25 rings were obtained from each aorta.

The rings were transferred immediately to serum-free medium and were washed extensively. Then, 24-well microliter plates were prepared by adding 300 microliters of collagen (Celltrix) per well, prepared as follows. Liquid collagen (7 volumes of 4 mg/ml solution) was mixed with 2 volumes of $NaHCO_3$ (11.7 mg./ml.) and 1 volume of lox minimal essential medium (MEM). Gelation occurred at 37° C. Following rinsing of the aortic rings, a second collagen mixture was prepared and 500 microliters were added to each well.

Immediately, one aortic ring was added to each well and physically oriented with a small disposable pipet tip so that it remained standing on edge.

After the gel had thickened partially (10–15 min.), the plate was transferred carefully to a 5% $CO_2$ incubator where the gel was allowed to harden (usually 30 min.), whereupon either EBB (endothelial cell basal medium, Clonetics) control medium, or EBB plus test sample, was added to each well. Test compounds were dissolved in absolute ethanol and 50 microliters were added to sterile PBS containing $Ca^{++}$ and $Mg^{++}$ with sonication. Samples were allowed to sonicate for 15 min., dilutions were made in PBS and finally in sterile EBB. Tristearin is a triglyceride with three C:18 fatty acyl side chains.

Experiments were performed and reproduced over 20 times during a six-month period. All reagents, media etc. were from the same stock solutions. In all cases, minimal cellular growth and migration occurred with PBS controls, as well as with many lipid controls. That was typified by fibroblast-type proliferation which began at about days 2–3 and continued for the duration of the assay (usually 8–10 days). The cells migrated well beyond the tissue explant but never assembled into microvessels.

Explants wherein microvessel growth was seen resembled the control explants at early time points and were typified by cellular proliferation and migration. However on or about the third day, cells (endothelial) began to spindle and elongate aligning themselves along a linear path. Fusion of the oriented cells formed obvious microtubles as early as the third day and at high magnification, inner lumen patency was observed.

Microvessel growth was scored using the following scale:

| | |
|---|---|
| Early microvessel growth with no bifurcations | 1 point |
| Early microvessel growth with one or two bifurcations | 2 points |
| Later microvessel growth (roughly twice as long as early growth vessel) with no bifurcations | 3 points |
| Later microvessel growth (roughly twice as long as early growth vessel) with one or two bifurcations | 4 points |

Aortic explants were observed thoroughly and scored each day, adding the cumulative points per explant and graphed as a function of total score per day. FIG. 1 depicts a typical assay. Maximal microvessel growth was elicited by the ATG-supplemented media, with a maximal microvessel score of nearly 250, representing an over 600% increase over control values.

Similarly, AMG showed a strong response. The PBS-supplemented media showed a minimal baseline microvessel growth of about 35 units. Tristearin, a common C:18 triglyceride, showed a similar minimal growth as obtained with the PBS control.

Other lipids were tested, all giving similar minimal growth. Among the negative lipids tested were: triglycerides (C:24, C:18, C:16, C:14 different permutations of substitutions); diglycerides (C:24, C: 18, C: 16, C: 14—different permutations of substitutions); monoglycerides (C:24, C:18, C:14); ceramide; cholesterol, sphingosine, cerebroside (galactosyl ceramide and glucosyl ceramide); phosphatidyl choline; phosphatidyl ethanolamine; and various glycosphingolipids (GM3, GD1a, globoside etc.). All the aforementioned lipids failed to show any significant growth induction as measured by endothelial cell growth, migration and tubule formation.

EXAMPLE 3

The in vivo angiogenic assay was conducted as follows. The method used was based on a model for testing anti-inflammatory activity of drugs in the cornea. (Arch. Opth. (1972) 88:308–313; Ben Ezra, D. (1978) "Neovasculogenic ability of prostaglandins, growth factors and synthetic chemoattractants." Am. J. Opthalmol. 86:455–461).

New Zealand rabbits weighing 3–4 pounds were anesthetized via an intramuscular injection of Ketamine (Provet) (100 mg.) and Xylazine (Provet) (20 mg.). The eye was kept open using a cotton applicator stick. One drop of Alcaine (proparacaine HCl, (Provet) was applied to the cornea and 50 microliters of a test compound dissolved in sterile PBS containing calcium and magnesium were injected interstromally between the inner and outer membranes of the cornea using a 30 gauge needle (1 cc. syringe). The degree of vascularization was assessed microscopically and macroscopically by direct visualization.

The experiments were performed over a six-month period and reproduced on 7 separate occasions involving over 300 rabbits. Scoring was based on the following criteria:

| | |
|---|---|
| 0–1 points | no visible response. |
| 2–3 points | reddening of the sclera and surrounding capillary bed of the limbus, but no apparent neovascularization or capillary outgrowth into the cornea |
| 4–6 points | slight pannus of neovascular growth into cornea, extending less than 10% into cornea, fading after 1–2 days |
| 7–10 points | substantial neovascular growth, comprising a pannus of capillary growth beginning at the limbus and extending into the cornea, with a division into the following categories: |
| 7 points | Directed growth toward injection focus, 20%–30% of distance from limbus to foci |
| 8 points | As above, 30%–50% |
| 9 points | 50%–75% |
| 10 points | 75%–100% |

Figure 2:
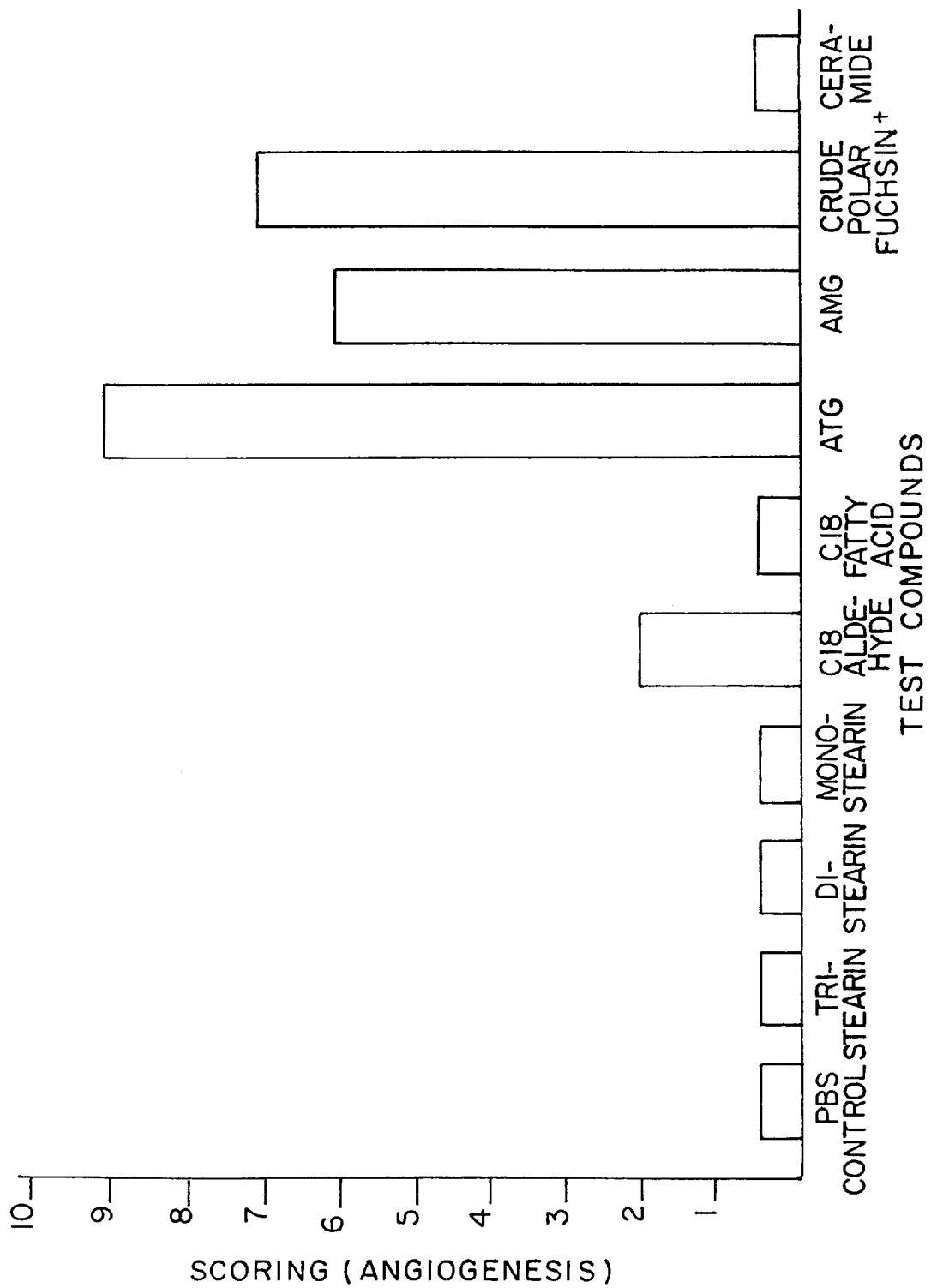
FIG. 2 depicts the effect various compounds have on vessel growth in vivo. AMG, ATG and PBS are as described for FIG. 1. C18 aldehyde is stearaldehyde. C18 fatty acid is stearic acid. Crude polar fuchsin$^+$ is a fraction of material obtained from the FLORISIL column. The ordinate depicts the degree of vessel growth.

FIG. 2 depicts a compilation taken from several different experiments. As can be seen readily, ATG and AMG gave remarkable angiogenic responses in the rabbit cornea. Another fraction, consisting of an as yet uncharacterized, fuschin-positive crude mixture, also gave a large angiogenic response. The fuschin+ crude mixture comprises polar lipid molecules obtained in the chloroform:methanol 2:1 fraction from the FLORISIL column. The mixture comprises molecules with fatty unsaturated ether linkage, molecules with a phosphate group and the like, such as a lysophosphatidyl glycerol compound. PBS and other lipid controls gave no response, except for some slight reddening of the sclera from $C_{18}$ aldehydes.

In nearly all cases of a positive response, scleral reddening and some corneal inflammation occurred at or about the 2nd day. The response usually cleared up at or about the 4th day, wherein a visible broad band of angiogenesis could be seen forming as bundles of outgrowths from the capillary system in the limbus. Importantly, in all cases, the angiogenesis was initiated from the portion of the limbus closest to induction site, and the direction of growth was maintained clearly as a vector toward the focus of injection, which could usually be seen even after a week as a light yellow, opaque dot.

EXAMPLE 4

The neuritogenesis assay was performed as follows. First, 24-well plates were coated with test compounds dissolved and diluted in ethanol, air-dried to rid of ethanol and washed once with sterile PBS. Neuroblastoma cells, such as PC12 cells obtained from ATCC, were seeded onto pre-coated 24-well plates at a density of $5 \times 10^5$ cells/ml.

Neuritogenesis was determined both qualitatively and quantitatively as follows. Assessment was made relative to positive control cells treated with nerve growth factor (NGF) (Boehringer-Mannheim). Neuritogenesis response was recorded as a daily plot of neuronal outgrowths/mm., determined by visually counting each new outgrowth. The assay was reproducible and proved to be an accurate method of quantification.

Figure 3:
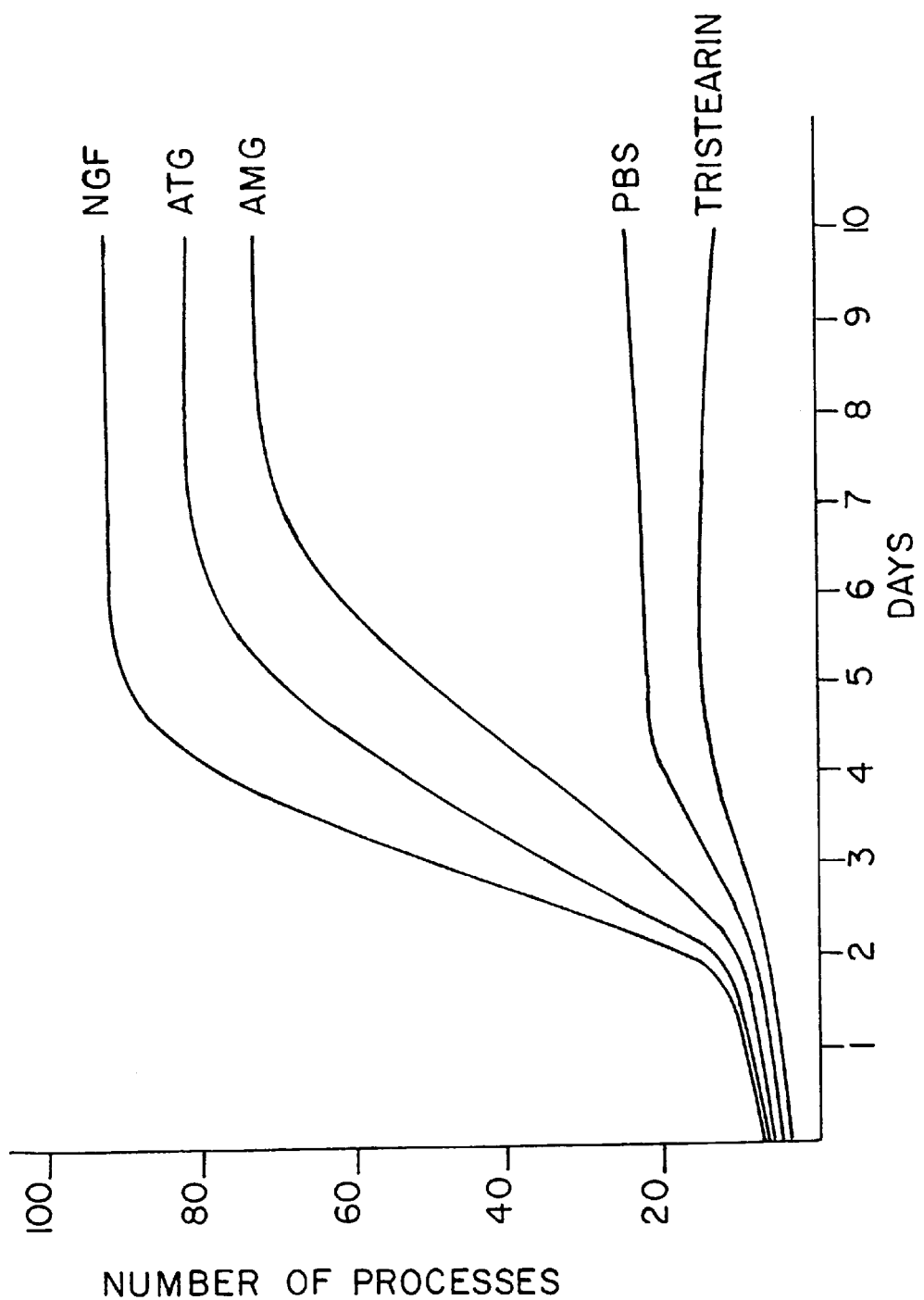
FIG. 3 depicts the effect various compounds have on PC12 cell growth. The abbreviations are as described for FIG. 1. NGF is nerve growth factor.

Scoring of neuritogenesis was accomplished by counting the individual neuritic processes extending outward from the cells. That data was graphed as a function of total processes per unit field over a period of 10 days. As can be seen from FIG. 3, a small percentage of spontaneous neuritogenesis was seen in all PBS controls, as well as with tristearin. All lipids tested, except for ATG and AMG gave similar low values as did the PBS control. ATG and AMG consistently stimulated neuritogenesis well above the negative control and comparable with the positive control (NGF).

EXAMPLE 5

The positive ion fast atom bombardment (+FAB) spectrum of ATG purified from human omentum, after treatment with $Na^{++}$ revealed several diagnostic features. The major diagnostic peak at 811 (M+Na+H) gives the molecular weight of 788 (811–23) That is supportive of ATG having C:16:16:16 chains with one unsaturation:

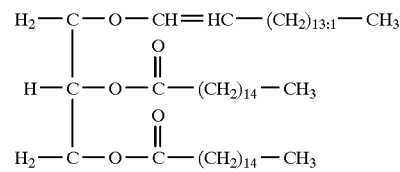

mw = 788

Positive FAB mass spectrometry of triglycerides and derivatives thereof typically do not yield stable molecular ions unless the sample is pretreated with $Na^{+2}$. Thus, in untreated samples, typically one will not find M+H, but when treated with $Na^{+2}$, will appear 23 mass units upfield.

Further evidence for that structure was offered by the predicted cleavage ion, 533, which represents the loss of one acyl group as an acid:

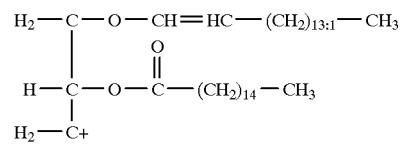

mw = 533

Finally, ATG was pre-treated with sodium methoxide, a base treatment which liberates all of the acyl linkages but will not cleave the vinyl ether group, and then scanned in the FAB. The sodium adduct gives 333 as the major ion, making the M+H=311, m.w.=310. That is consistent with a C:16 mono-alkenyl glyceride with two unsaturations in the carbon backbone:

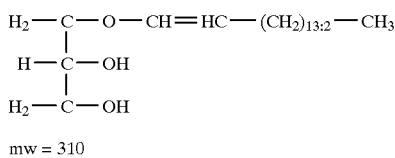

mw = 310

Further data revealed that as the 311 ion is present, the 293 ion is diagnostic for loss of a water molecule therefrom:

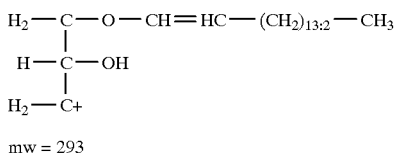

mw = 293

EXAMPLE 6

Evidence for a series of ATG molecules was obtained after hydrogenation of ATG over Pd catalyst. That process revealed a number of ions diagnostic for ATG molecules with various chain lengths. For example,

| ion | Na$^{++}$ |   | mw | carbon side chain lengths |
|-----|-----------|---|-----|---------------------------|
| 955 | − 23      | = | 932 | 18:20:20 |
| 927 | − 23      | = | 904 | 18:18:20 |
| 899 | − 23      | = | 876 | 18:18:18 |
| 871 | − 23      | = | 848 | 16:18:18 |
| 843 | − 23      | = | 820 | 16:16:18 |
| 815 | − 23      | = | 792 | 16:16:16 |

The following cleavage ions, as found in the native hydrogenated spectrum, are diagnostic for the corresponding alkenyl-acyl diglyceride (note, 17 is added to compensate for loss of water):

| ion | H$_2$O |   | mw | carbon chain |
|-----|--------|---|-----|--------------|
| 621 | +  17  | = | 638 | 18:20 |
| 593 | +  17  | = | 610 | 18:18 |
| 565 | +  17  | = | 582 | 16:18 |
| 537 | +  17  | = | 554 | 16:16 |
| 509 | +  17  | = | 526 | 14:16 |

Also, mono-alkenyl diagnostic ions can be found as follows:

| ion | H$_2$O |   | mw | carbon chain |
|-----|--------|---|-----|--------------|
| 353 | +  17  | = | 370 | C:20 |
| 297 | +  17  | = | 317 | C:16 |
| 267 | +  17  | = | 284 | C:14 |

A C:18 mono-alkenyl ion was not found because the large ion at 341 representing the C:18 mono-acyl cleavage product likely is more stable than the corresponding alkenyl molecule.

EXAMPLE 7

The native spectrum of AMG from omentum gives M+H= 341, m.w.=340, and the sodium adduct confirms that as the molecular weight 340+23=363 (and 365), as the major ion (also 385 with two sodium adducts). 340 and 343 predicts mono-alkenyl glyceride: C:18, C18:1.

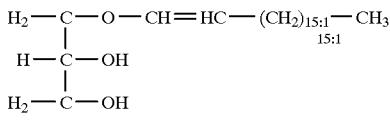

mw = 342; 18:1 = 340

EXAMPLE 8

A nearly identical spectrum was obtained for AMG isolated from placenta. The native compound gives M+H as 341 and 343, m.w.=340 and 342. That is confirmed by sodium adduct ions, 363 and 365 (as well as two sodium adducts 385 and 387). The structure for the placental AMG is:

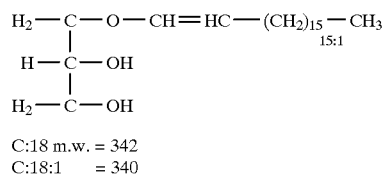

C:18 m.w. = 342
C:18:1    = 340

EXAMPLE 9

Bovine brain ethanolamine glycerophospholipids (commercially available, for example, Sigma, or obtainable in gram quantities by known methods) are de-acylated by alkaline methanolysis with excess 0.5 N methanolic NaOH. NaOH is added to the dissolved lipids in chloroform for 1 hr. at 23 degrees C. The reaction is stopped by addition of 1 N acetic acid until neutral pH is reached and the reaction mixture is gently mixed in a separatory funnel. After equilibration, the lower phase is collected and dried under vacuum at room temperature.

The resultant lipid oil is dissolved in a minimal amount of chloroform, centrifuged and applied to a 10 micron Iatrobead (Iatron, Tokyo) HPLC column (2×100 cm.) and a gradient is applied from 100% chloroform to 100% methanol. Lysoplasmenylethanolamine (LPE) is obtained at near homogeneity.

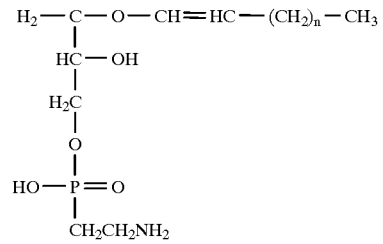

EXAMPLE 10

To obtain ANG, LPE is treated with phospholipase C (commercially available or obtainable by known methods), which cleaves the phosphatidyl group at the proximal oxygen. The resultant AMG is purified by Iatrobead HPLC employing a 100% toluene to acetone-ether (80:20) gradient.

EXAMPLE 11

To obtain ADG, protection of LPE first is accomplished by blocking the polar phosphatidyl functional group using an N-9-fluorenylmethoxylcarbonyl (Fmoc) protection group (standard in the literature). The resultant derivative is purified as described above using a chloroform to methanol HPLC gradient.

To acylate, the protected LPE is dried under anhydrous conditions and after addition of DMAP, the appropriate fatty acyl anhydride or acyl chloride is added in molar excess and the reaction mixture stirred for 10 hours at 30° C. Dicyclohexylcarbodiimide is added throughout to regenerate the anhydride. The reaction is terminated by addition of diethylamine.

The resultant plasmenylethanolamine (PPE) is purified on an Iatrobeads HPLC column using a hexane-isopropanol-water-ammonium hydroxide gradient. The ADG is obtained by treating the PPE with phospholipase C, yielding the typical hydroxyl group of glycerol. The resultant ADG is purified by Iatrobead HPLC employing a 100% tolune to hexane-ether (50:50) gradient.

EXAMPLE 12

To obtain ATG, AMG is acylated directly with the appropriate fatty acyl anhydride or acyl chloride as described in the previous Examples and the resultant ATG is purified by Iatrobead HPLC employing a 100% toluene to hexane-diethyl ether (80:20) gradient.

All references recited herein are incorporated in entirety.

While the invention has been described in detail and with reference to certain embodiments thereof, it would be apparent to one skilled in the art that various changes and modifications can be made without departing from the spirit and scope thereof.

What is claimed:

1. A pharmaceutical composition comprising an angiogenic effective amount of an isolated alk-1-enyl glycerol derivative of the formula:

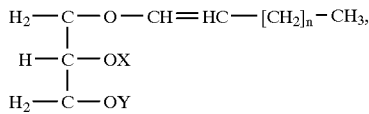

wherein n is 0–23 and X and Y are independently H or an acyl group having from 2 to 26 carbon atoms, and a pharmaceutically acceptable carrier, diluent or exipient.

2. The pharmaceutical composition of claim 1, wherein n is 13 or 15.

3. The pharmaceutical composition of claim 1, wherein X is an acyl group and Y is H.

4. The pharmaceutical composition of claim 3, wherein said acyl group comprises 20 carbon atoms.

5. The pharmaceutical composition of claim 4, wherein said 20 carbon atom acyl group is an arachidonate group.

6. The pharmaceutical composition of claim 1, wherein X and Y are acyl groups.

7. The pharmaceutical composition of claim 6, wherein Y comprises 20 carbon atoms.

8. The pharmaceutical composition of claim 7, wherein said 20 carbon atom acyl group is an arachidonate group.

9. The pharmaceutical composition of claim 7, wherein X is an acyl group comprising 16 or 18 carbon atoms.

10. The pharmaceutical composition of claim 8, wherein X is an acyl group comprising 16 or 18 carbon atoms.

11. The pharmaceutical composition of claim 1, wherein X and Y are both H.

12. The pharmaceutical composition of claim 11, wherein n is 13 or 15.

13. The pharmaceutical composition of claim 1, wherein Y is an acyl group and X is a H.

14. The pharmaceutical composition of claim 13, wherein said acyl group comprises 20 carbon atoms.

15. The pharmaceutical composition of claim 14, wherein said 20 carbon atom acyl group is an arachidonate group.

16. A pharmaceutical composition comprising an angiogenic effective amount of an isolated alk-1-enyl glycerol derivative of the formula:

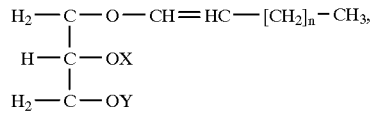

wherein n is 0–23 and X and Y are independently H or an acyl group having from 2 to 26 carbon atoms, a pharmaceutically acceptable carrier, diluent or excipient and a potentiator, wherein the potentiator stimulates activity of the alk-1-enyl glycerol derivatives.

17. The pharmaceutical composition of claim 16, wherein n is 13 or 15.

18. The pharmaceutical composition of claim 16, wherein X is an acyl group and Y is H.

19. The pharmaceutical composition of claim 18, wherein said acyl group comprises 20 carbon atoms.

20. The pharmaceutical composition of claim 19, wherein said 20 carbon atom acyl group is an arachidonate group.

21. The pharmaceutical composition of claim 16, wherein X and Y are acyl groups.

22. The pharmaceutical composition of claim 21, wherein Y comprises 20 carbon atoms.

23. The pharmaceutical composition of claim 22, wherein said 20 carbon atom acyl group is an arachidonate group.

24. The pharmaceutical composition of claim 22, wherein X is an acyl group comprising 16 or 18 carbon atoms.

25. The pharmaceutical composition of claim 16, wherein X and Y are both H.

26. The pharmaceutical composition of claim 25, wherein n is 13 or 15.

27. The pharmaceutical composition of claim 16, wherein Y is an acyl group and X is a H.

28. The pharmaceutical composition of claim 27, wherein said acyl group comprises 20 carbon atoms.

29. The pharmaceutical composition of claim 28, wherein said 20 carbon atom acyl group is an arachidonate group.

30. The pharmaceutical composition of claim 16, wherein the potentiator is a glycerol phospholipid or a disialyl ganglioside.

31. The pharmaceutical composition of claim 30, wherein the potentiator is a disialyl ganglioside.

32. The pharmaceutical composition of claim 31, wherein said disialyl ganglioside is $GD_3$.

33. The pharmaceutical composition of claim 16, wherein the potentiator is a glycerol phospholipid.

34. The pharmaceutical composition of claim 33, wherein said glycerol phospholipid is lysophosphatidyl serine.

35. The pharmaceutical composition of claim 33, wherein X and Y are both H and n is 13 or 15.

* * * * *